(12) United States Patent
Majeed et al.

(10) Patent No.: US 7,014,874 B1
(45) Date of Patent: Mar. 21, 2006

(54) **COMPOSITIONS AND METHODS CONTAINING *ALLIUM SATIVUM* LINN. (GARLIC) NATURALLY ENRICHED WITH ORGANIC SELENIUM COMPOUNDS FOR NUTRITIONAL SUPPLEMENTATION**

(75) Inventors: Muhammed Majeed, Piscataway, NJ (US); Rajinder Kumar Bammi, Bangalore (IN); Vladimir Badmaev, Piscataway, NJ (US); Subbalakshmi Prakash, Piscataway, NJ (US); Nagabhushanam Kalyanam, Piscataway, NJ (US)

(73) Assignee: Sami Labs Limited, Bangalore (IN)

( * ) Notice: Subject to any disclaimer, the term of this patent is extended or adjusted under 35 U.S.C. 154(b) by 12 days.

(21) Appl. No.: 10/605,578

(22) Filed: Oct. 9, 2003

Related U.S. Application Data (63) Continuation-in-part of application No. 10/249,239, filed on Mar. 25, 2003.

(60) Provisional application No. 60/367,274, filed on Mar. 26, 2003.

(51) Int. Cl.
*A61K 35/78* (2006.01)

(52) U.S. Cl. ........................... 424/754; 424/725

(58) Field of Classification Search ............... 424/754, 424/773, 195.1, 725
See application file for complete search history.

(56) References Cited

OTHER PUBLICATIONS

Kotrebai et al. Selenium Speciation in Enriched and Natural Samples by HPLC-ICP-MS and HPLC-ESI-MS with Perfluorinated Carboxylic Acid Ion Pairing Agents; Analyst (2000) 125, pp. 71-78.*

McSheehy et al. Speciation Analysis of Selenium in Garlic by Two Dimensional High Performance Liquid Chromatography with Parallel Inductively Coupled Plasma Mass Spectrometric and . . . Analytica Chimica Acta, Iss.2, (2000) pp. 147-153 (pp. 1-9 print out).*

* cited by examiner

*Primary Examiner*—Patricia Leith

(57) ABSTRACT

The invention discloses a method to prepare concentrates from *Allium sativum* Linn. (Garlic) bulbs naturally enriched with an unique composition of organic selenium compounds and the use of such concentrates in nutritional supplement compositions for human and animal use. The resulting compositions provide a safe and efficacious means of providing supplemental amounts of the essential trace mineral nutrient selenium for diverse health benefits.

1 Claim, 7 Drawing Sheets

L-Selenomethionine      γ-Glutamyl-L-Selenomethionine

Se-methyl-L-selenocysteine   γ-Glutamyl-Se-methyl-L-selenocysteine

Chemical structures of the organic selenium compounds in the composition

L-Selenomethionine  γ-Glutamyl-L-Selenomethionine

Se-methyl-L-selenocysteine  γ-Glutamyl-Se-methyl-L-selenocysteine

Figure 1: Chemical structures of the organic selenium compounds in the composition Figure 2: Plasma lipid peroxidation Figure 3: Glutathione S-transferase Figure 4: Superoxide Dismutase

Figure 5: Catalase

Figure 6: Liver Function Parameters

KIDNEY FUNCTION PARAMETERS

Figure 7: Kidney Function Parameters

COMPOSITIONS AND METHODS CONTAINING *ALLIUM SATIVUM* LINN. (GARLIC) NATURALLY ENRICHED WITH ORGANIC SELENIUM COMPOUNDS FOR NUTRITIONAL SUPPLEMENTATION

CROSS REFERENCE TO RELATED APPLICATIONS

This application claims the benefit of U.S. Provisional patent application No. 60/367,274 filed on Mar. 26, 2002, and is a continuation-in-part of U.S. patent application Ser. No. 10/249,239, filed on Mar. 25, 2003 the disclosure of which is hereby incorporated by reference.

BACKGROUND OF INVENTION

The present invention is related to compositions and methods containing *Allium sativum* Linn. bulbs naturally enriched with organic selenium compounds, and the use of these compositions for nutritional supplementation in animals and humans.

The parent application disclosed a novel process for preparing garlic bulbs naturally enriched with an unique composition of organic selenium compounds through a soilless culture technique. The details of the composition were also disclosed. The current invention further improved upon the composition of the parent application by enabling the preparation of a concentrate containing the unique composition of organic selenium compounds disclosed in the parent application, in specific proportions, for nutritional supplementation in humans and animals.

Selenium is a vital trace element nutrient with multiple roles in the growth and functioning of living cells in higher animals and humans. At the molecular level, selenium (as selenocysteine) is an essential component of the active sites of the antioxidant enzyme glutathione peroxidase, and the enzymes participating in thyroid functions iodothyronine-5'-deiodinase and mammalian thioredoxin reductase. Selenium is also present in several other mammalian selenoproteins. Low selenium status has been linked with the occurrence of decreased immunity to diseases and the prevalence of various forms of cancer.

Selenium occurs in foods, through uptake by plants from the soil, in the form of the selenoamino acids, selenomethionine and selenocysteine, and their derivatives. However, as the element is unevenly distributed in the earth's crust, dietary supplementation is often needed. Organic selenium compounds are preferred for supplementation on account of their superior bioavailability. An ideal nutritional supplement would be a selenium enriched edible plant part wherein the selenium metabolically accumulates in the form of bioavailable organic selenium compounds. Plants that naturally contain higher levels of the sulfur containing amino acids such as those from the *Allium* and *Brassica* species are preferred for enrichment, based on metabolic criteria. Selenium-enriched garlic is reported to be useful as a nutritional supplement in the prevention of cancer (Ip, et al., 1992, 1996; Ip and Lisk, 1993, 1997; Lu et al., 1996).

Clinical intervention trials and in vitro data revealed the efficacy of selenium in the form of selenium yeast or selenomethionine in cancer prevention (Clark et al., 1996, 1998). Ip et al (2000) described the role of chemical speciation on the comparative activity of selenium-enriched garlic and selenium yeast in mammary cancer prevention in rats, wherein selenium-enriched garlic was shown to be more efficacious than selenium yeast. γ-glutamyl Se-methylselenocysteine is reported to be the major form of selenium in selenium-enriched garlic while L-Selenomethionine was shown to be the major form of selenium in selenium enriched yeast.

Laboratory studies indicate that γ-Glutamyl-Se-methyl-L-selenosysteine is an effective chemopreventive agent, serving as a carrier for Se-Methyl-L-selenocysteine (Dong et al., 2001; Medina et al., 2001). Se-Methyl-L-selenocysteine is a well researched chemopreventive organoselenium compound, which is not incorporated in the body proteins, and is therefore less toxic than other forms of supplemental selenium (Ip et al., 1994; Medina et al., 2001).

The following is a list of literature cited in this application, each of which is hereby incorporated by reference in its entirety: 1. Ip, C., Lisk, D. J, and Stoewsand, G. S. 1992. "Mammary Cancer prevention by Regular Garlic and Selenium-Enriched Garlic." Nutr. Cancer 17, 279–286. 2. Ip.C, and .Lisk, D. J. 1996. "The attributes of Selenium Enriched Garlic in Cancer Prevention." In Dietary Phytochemicals in Cancer Prevention and Treatment 15, 179–187. 3. Ip. C, and Donald, J. Lisk. 1993. "Bioavailability of Selenium From SeleniumEnriched Garlic." Nutr. Cancer 20, 129–137. 4. Ip, C and Lisk, D. J. 1997. "Modulation of phase I and Phase II Xenobiotic-metabolizing Enzymes by Enriched Garlic in rats." Nutr. and Cancer 28(2), 184–188. 5. Lu., J., Pei H., Ip C., Lisk D J., Ganther H and Thompson H J., 1996. Effect on an aqueous extract of selenium enriched garlic on in vitro and in vivo efficacy in cancer prevention. Carcinogenesis, 17(9): 1903 1907. 6. Ip, C; Ganther, H. Novel Strategies In Selenium Cancer Chemoprevention Research; In Selenium In Biology and Human Health; Burk, R. F. Ed; (1994) Springer-Verlag, New York: 169 180. 7. Ip. C., Birringer, M., Block, E., Kotrebai, M., Tyson, J. F., Uden, P. C., and Lisk, D. J. 2000. Chemical Speciation Influences Comparative Activity of Selenium-Enriched Garlic and Yeast in Mammary Cancer Prevention. J. Agric. Food Chem. 48, 2062–2070 8. Dong, Y. et al. 2001 Characterization and Biological Activity of γ-Glutamyl-Se Methylselenocysteine: A Novel, Naturally Occurring Anticancer Agent From Garlic. Cancer Res. 61:2923–2928. 9. Medina, D. et al. 2001 Se-Methylselenocysteine: A new compound for chemoprevention of breast cancer. Nutrition and Cancer 40(1):12–17. 10 Clark L C, et al. 1996 Effects of selenium supplementation for cancer prevention in patients with carcinoma of the skin. A randomized controlled trial. Nutritional Prevention of Cancer Study Group. JAMA. 276(24):1957–63. 11. Clark, LC et al. Inhibitory effect of selenomethionine on the growth of three selected human tumor cell lines. Cancer Lett. 1998 Mar. 13; 125(1–2): 103–10.

SUMMARY OF INVENTION

The invention discloses a method to prepare concentrates from *Allium sativum* Linn. (Garlic) bulbs naturally enriched with an unique composition of organic selenium compounds and the use of such concentrates in nutritional supplement compositions for human and animal use. The resulting compositions provide a safe and efficacious means of providing supplemental amounts of the essential trace mineral nutrient selenium for diverse health benefits. Toxicological studies revealed that the $LD_{50}$ of the composition in rats is greater than 2000 mg/kg body weight.

Supplementation with the composition of the invention produced positive improvement in antioxidant profile in human subjects with no adverse effects. Antioxidant profile refers to the levels of lipid oxidation products (lipid peroxides) and the levels of protective antioxidant enzymes (Glutathione-S-transferase, Superoxide dismutase and Catalase) in the plasma of the subjects. Glutathione S-transferase (GST) is a key detoxicant enzyme that removes toxic substances in the body, through conjugation with glutathione or reduction by glutathione peroxidase.

DETAILED DESCRIPTION

The invention discloses a method to prepare a concentrate containing a defined composition of organic selenium compounds from *Allium sativum* Linn (garlic) which has been enriched with selenium by a soilless culture method. A supercritical extraction process is employed to concentrate the organic selenium compounds followed by separation using chromatographic methods. The compounds separated consist of the Selenoamino acids L-Selenomethionine and Se-Methyl-L-selenocysteine; and Selenoamino acid dipeptides, N-γ(L-Glutamyl) L-selenomethionine-N-γ(L-Glutamyl) Se-methyl-L-selenocysteine. A dispersion of these compounds is made in natural garlic powder containing 10 to 500 ppm of Alliin, for nutritional supplementation.

EXAMPLE 1

Process to Prepare a Composition Containing Selectively Fractionated Bioactive Organic Selenium Compounds from Selenium-Enriched *Allium sativum* Linn Bulbs 100 kg of selenium-enriched garlic bulbs prepared by soilless culture technique were crushed and subjected to multi-stage supercritical fluid extraction followed by chromatographic separation. High pressure carbon dioxide (10 to 60 MPa), modified with ethanol and water (50:50), was used to extract Selenium containing non-protein amino acids as well as selenoamino acid dipeptides. These were separated and purified using preparative HPLC, the mobile phase and water were removed by evaporation under reduced pressure and freeze drying, to yield bioactive selenoamino acid and selenoamino acid dipeptide fractions.

The fractions obtained were blended with natural garlic powder to yield a composition containing 100 to 2000 ppm of selenium in the form of organic selenium compounds. The composition of the selenium enrichment concentrate configured to provide 1000 ppm organic selenium content in natural garlic powder containing 200 ppm Alliin is detailed in Table 1.

TABLE 1

Composition of Enrichment Concentrate

| Compound | Concentration | Elemental Selenium |
|---|---|---|
| N-γ(L-Glutamyl)Se-methyl-L-selenocysteine | 1340 ppm | 340 ppm |
| N-γ(L-Glutamyl)L-selenomethionine | 40 ppm | 10 ppm |
| L-Selenomethionine | 125 ppm | 50 ppm |
| Se-Methyl-L-selenocysteine | 1385 ppm | 600 ppm |

EXAMPLE 2

Toxicological Studies on the Selenium Enriched Garlic Powder

The study was designed to determine the acute oral toxicity of garlic powder enriched with the mixture of Example 1 to Sprague Dawley rats (male and female) of age 6 to 8 weeks with weight ranging from 124.1 g to 140.6 g. They were randomly selected in groups of five of like sex at the time of initiating the study.

The test substance suspended in water was administered by oral route to rats, at a dose volume of 10 ml/kg. Ten rats (5 male and 5 female) were allocated to a treatment of 2000 mg/kg of the test composition. The rats were observed for 14 days after treatment. All animals survived through the study period of 14 days and were free of intoxicating signs 1 to 2 hours after the treatment. The $LD_{50}$ value of the composition in rats by oral route was found to be greater than 2000 mg/kg body weight.

EXAMPLE 3

Clinical Efficacy and Safety of the Composition

Study Objective: To determine the efficacy and safety of the composition in reducing oxidative stress levels.

Study Design: 42-day open prospective single centre study to measure the efficacy and safety of composition. In this 42 day study, each patient was administered the composition (providing 100 mcg of selenium) in a single dose, daily after a meal. Selection of Subjects: The selection criteria stipulated were that the subjects have a BMI (body mass index) of 20–38 kg/m2, fall in the age group of 35 to 60 years, with an increased risk of heart disease. These subjects would be otherwise in good health, with no history of alcohol or drug abuse, and no known allergies. Kidney and liver functions would be normal. 13 subjects (in the age group of 25 to 43 years (6 males and 7 females)), participated in the study.

Study Procedures: Efficacy was assessed based on change in oxidative stress, as evidenced by measuring antioxidant profile. Safety was assessed based on standard liver function and kidney function tests. Adverse events, if any, were recorded. Liver function is assessed by using specific enzyme markers. For example, both SGPT (Serum Glutamate-Pyruvate Transaminase) and SGOT (Serum Glutamate-Oxaloacetate Transaminase) are important in the clinical diagnosis of disease. These enzymes, particularly abundant in heart and in liver, are released from injured cells in myocardial infarction, infections, liver damage or cardiovascular disease. Kidney function tests seek to evaluate how well the kidneys filter and transport metabolic waste from the blood into the urine. Serum creatinine, serum urea, and electrolyte (sodium, potassium and chloride) levels are measured. ESR (Erythrocyte sedimentation Rate) and haemoglobin levels, if abnormal, provide an indication of the presence of disease.

Figure 1:
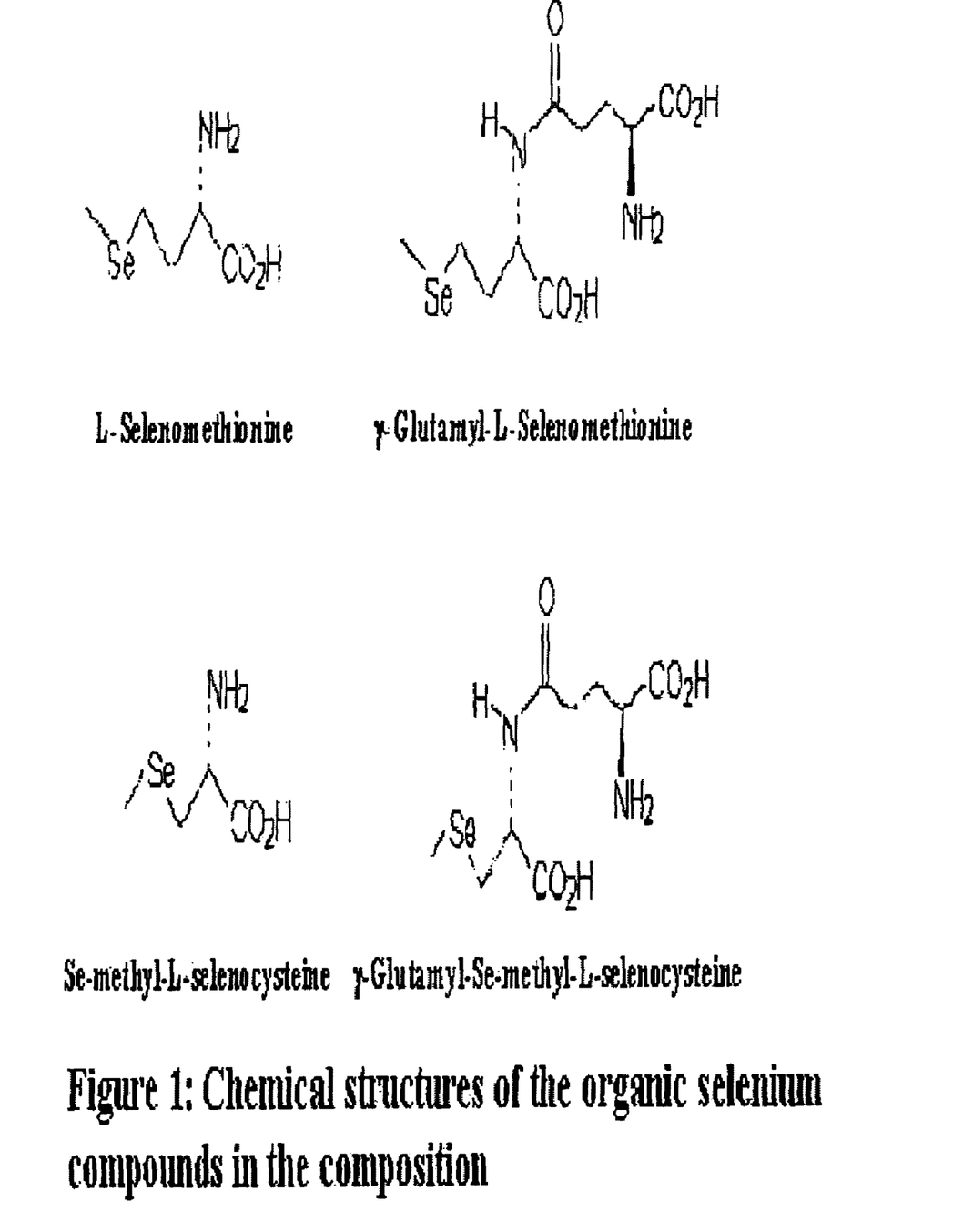
FIG. 1 shows the chemical structures of organic selenium compounds in the composition
Figure 2:
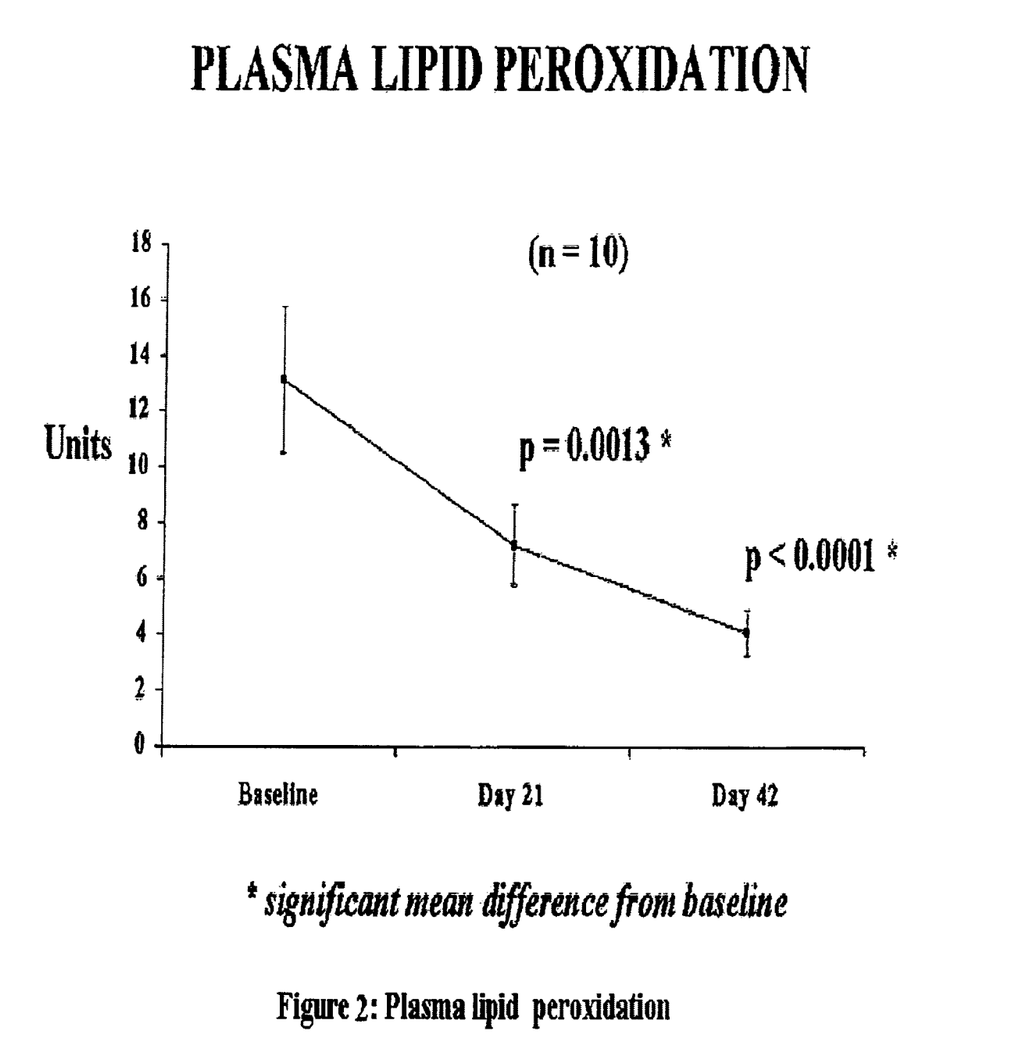
FIG. 2 shows the effects of supplementation with the composition on plasma lipid peroxidation in human subjects
Figure 3:
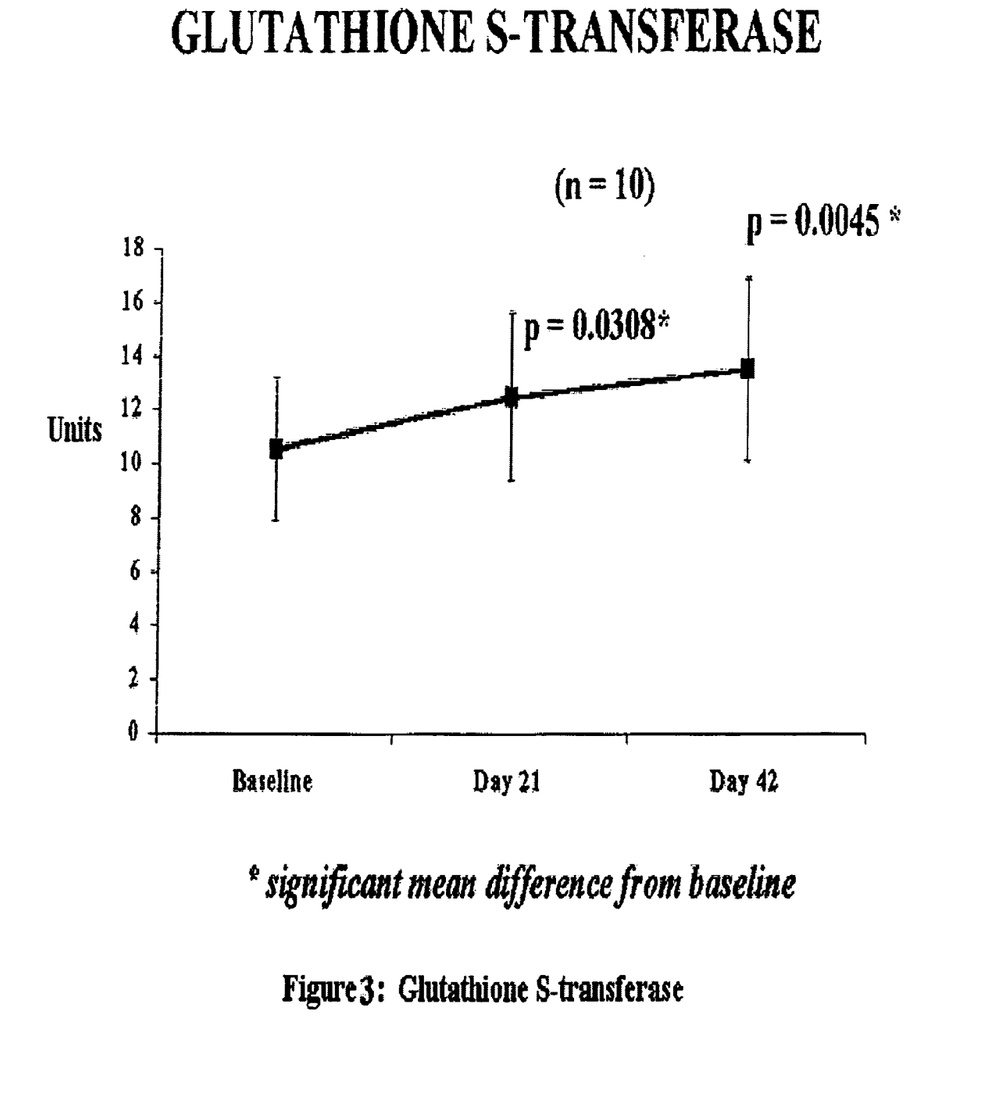
FIG. 3 shows the effects of supplementation with the composition on glutathione peroxidase levels in human subjects.
Figure 4:
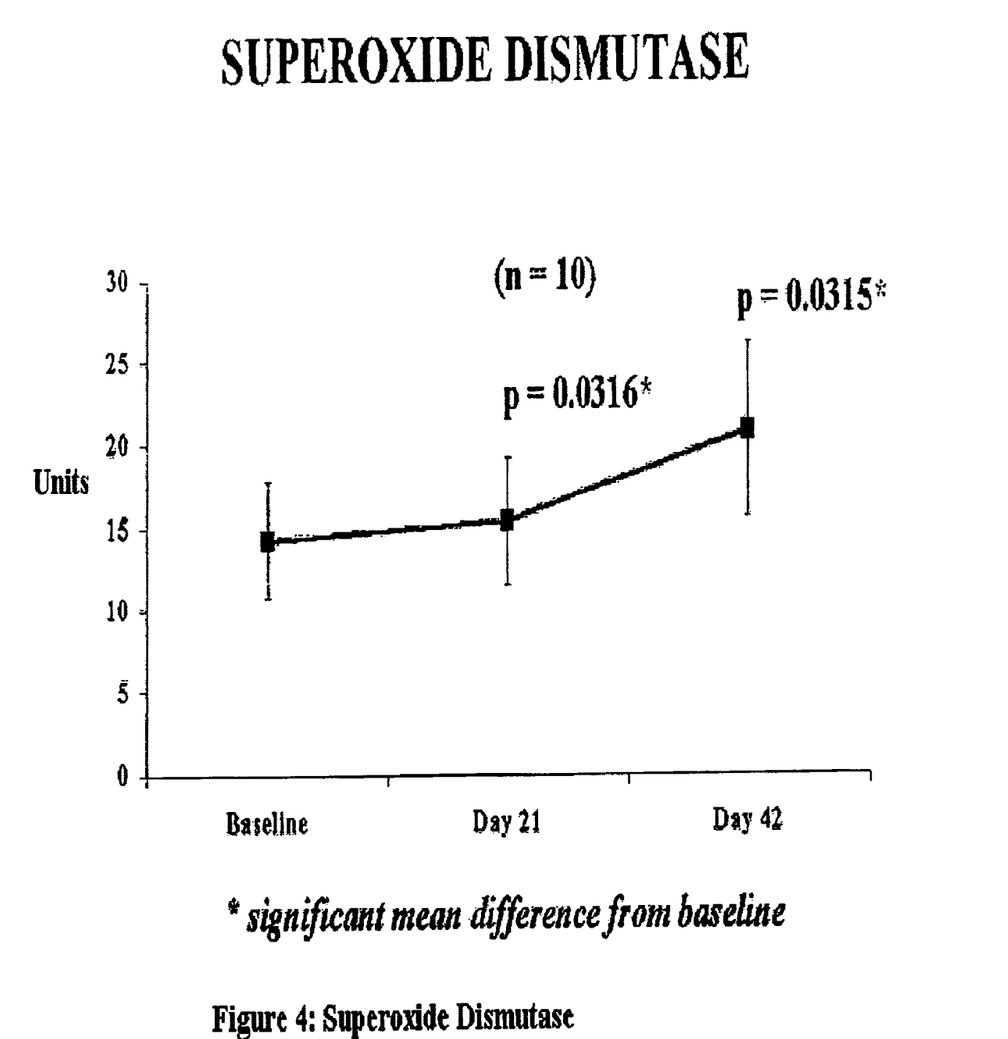
FIG. 4 shows the effects of supplementation with the composition on superoxide dismutase activity in human subjects
Figure 5:
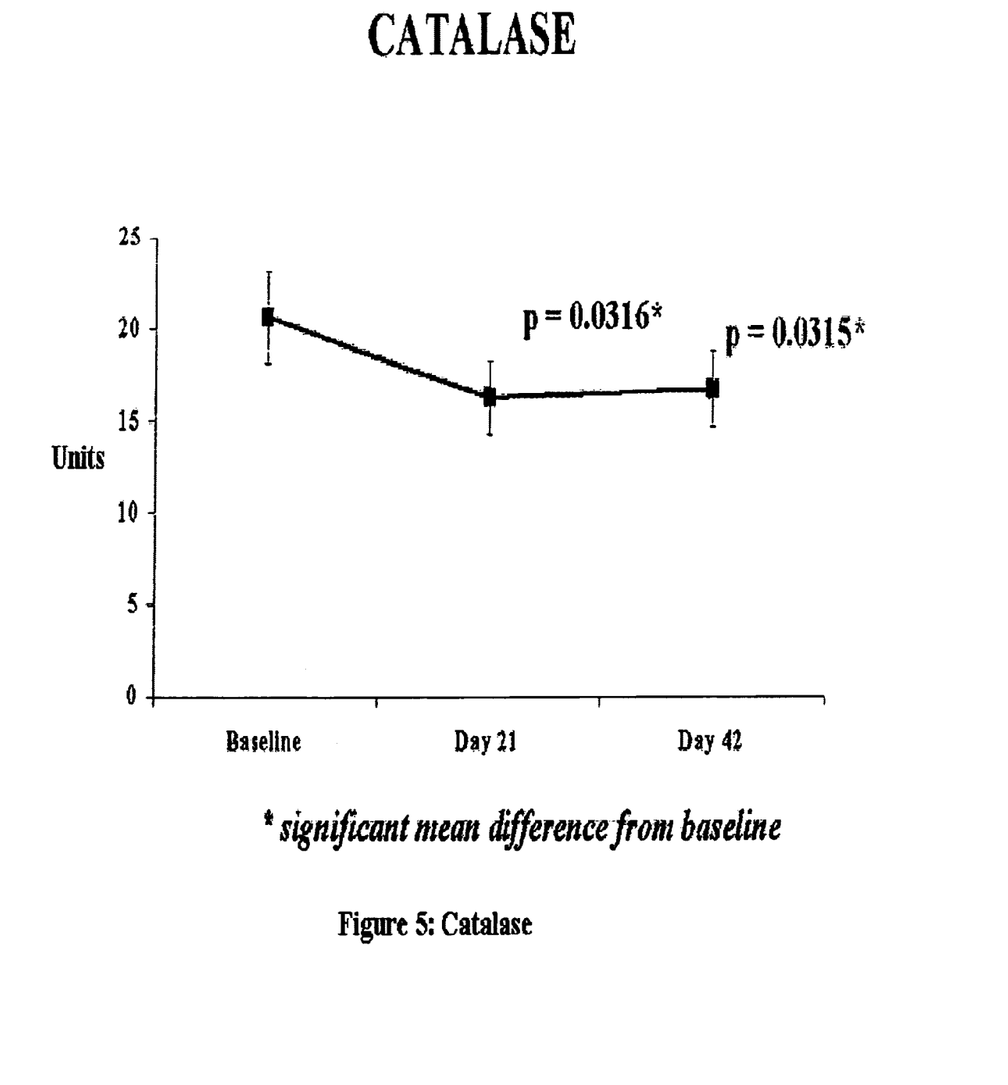
FIG. 5 shows the effects of supplementation with the composition on catalase activity in human subjects

Results: Efficacy: From day 0 (baseline) to day 21, and from day 0 to day 42, plasma lipid peroxidation reduced by an average of 5.39 units and 9.28 units respectively. Both decreases were statistically significant (FIG. 2). Lymphocyte antioxidant count for Glutathione-S-transferase and Superoxide dismutase were found to increase from day 0 to day 21, and from day 0 to day 42. The Catalase values decreased during this period. All the mean differences from baseline were found to be statistically significant (FIGS. 3–5).

Figure 6:
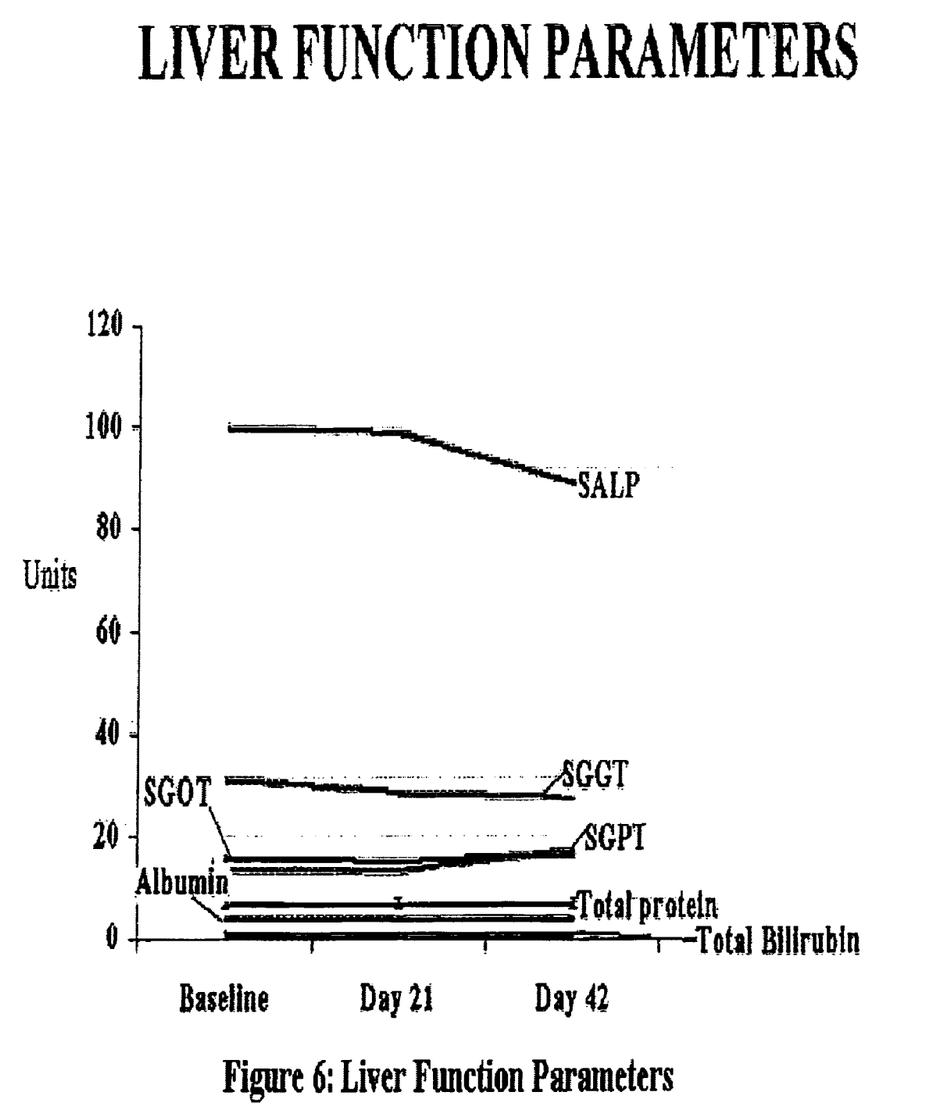
FIG. 6 shows that supplementation with the composition for 42 days produced no adverse effects on liver function parameters in human subjects
Figure 7:
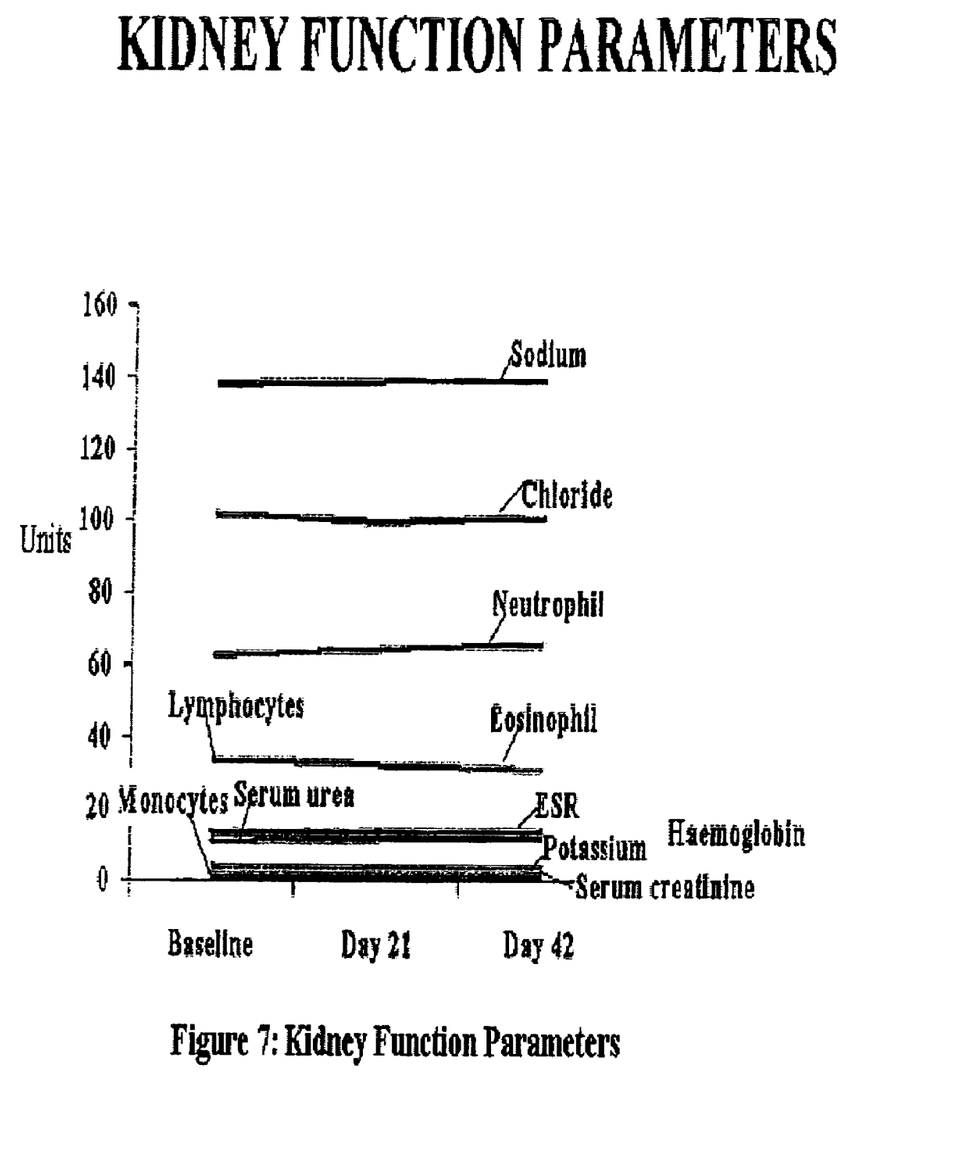
FIG. 7 shows that supplementation with the composition for 42 days produced no adverse effects on kidney function parameters in human subjects

Safety: The laboratory values of parameters for liver function and kidney function were found to be within admissible limits, with minor changes reported during the course of the study. The variation was within 5% of normal values (FIGS. 6 and 7). Similarly blood lipid profiles remained within the normal range. No adverse events were observed in any of the subjects or reported during the study.

Conclusions: The results of this open prospective clinical study suggest that the composition effectively reduces oxidative stress levels, and is safe for use as an antioxidant nutritional supplement.

While an exemplary embodiment of the composition and its use is presented in the current invention, the intention is to cover all modifications and alterations falling within the scope of the appended claims.

What is claimed is:

1. A method for preparing an enrichment concentrate of organic selenium compounds consisting of the following steps:
    (1) crushing selenium enriched garlic bulbs;
    (2) supercritical extraction of said bulbs with carbon dioxide wherein said extraction is modified with a solvent selected from ethanol, ethyl acetate, water, or a mixture of ethanol and water;
    (3) separation of individual organic selenium compounds using preparative high performance liquid chromatography (HPLC) to produce fractions containing individual organic selenium compounds; and
    (4) obtaining said fractions from step (3) and blending said fractions with garlic powder.

* * * * *